United States Patent [19] [11] 3,931,196
Swan [45] Jan. 6, 1976

[54] PHOSPHINOLINES AND PHOSPHINDOLINES
[75] Inventor: John Melvin Swan, Canterbury, Australia
[73] Assignee: Monash University, Clayton, Australia
[22] Filed: Feb. 26, 1973
[21] Appl. No.: 335,760

[30] Foreign Application Priority Data
Feb. 28, 1972 Australia............................ 8109/72
May 31, 1972 Australia............................ 9157/72

[52] U.S. Cl........ 260/293.62; 260/247; 260/247.1 B; 260/326.61; 260/543 P; 260/570.5 R; 260/570.5 S; 260/606.5 P; 424/200; 424/209; 260/502.4 R; 260/936
[51] Int. Cl.² ............................................. C07F 9/53
[58] Field of Search..... 260/247.1 B, 247 S, 293.62, 260/326.61, 239 R, 570.5 R, 570.5 S

[56] References Cited
UNITED STATES PATENTS
3,442,948  5/1969  Wiley............................ 260/570.5 R
3,505,404  4/1970  Peterson et al................. 260/570.8 R
3,632,649  1/1972  Maier........................... 260/570.5 R Primary Examiner—Lorraine A. Weinberger
Assistant Examiner—Michael Shippen
Attorney, Agent, or Firm—Haseltine, Lake & Waters

[57] ABSTRACT
This invention is for phosphinoline and phosphindoline compounds having the formula,

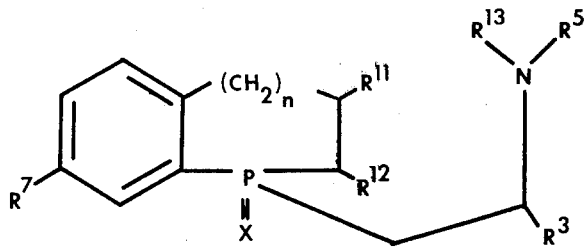

wherein $n$ is 0 or 1; X is 0 or S; $R^3$ is hydrogen or methyl; $R^5$ is hydrogen or methyl, or may be bound to $R^{13}$ to form a morpholino, piperidino or pyrrolidino ring; $R^7$ is hydrogen or hydroxy; $R^{11}$ and $R^{12}$ are hydrogen; $R^{13}$ is methyl, or $R^{13}$ and $R^5$ may be joined together as above stated to form a morpholino, piperidino, or pyrrolidino ring. The compounds are analgesics.

8 Claims, No Drawings

PHOSPHINOLINES AND PHOSPHINDOLINES

This invention relates to chemical compounds which possess useful physiological, especially analgesic properties, and to processes for the preparation of these compounds.

The compounds of the present invention are phosphines, phosphine oxides and phosphine sulphides of the general formula (1),

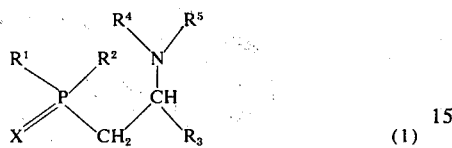

(1)

in which
- $R^1$ = aryl or substituted aryl;
- $R^2$ = aryl, substituted aryl, alkyl, or substituted alkyl; when $R^2$ is alkyl or substituted alkyl, then $R^1$ and $R^2$ may together form a ring;
- $R^3$ = H, or lower alkyl;
- $R^4$ = H, or alkyl, and when $R^2$ is alkyl or substituted alkyl, $R^2$ and $R^4$ may together form a ring;
- $R^5$ = H, alkyl, aralkyl, and may be joined to $R^4$, optionally through an oxygen atom, to form a ring;
- X = a lone pair of electrons, O, S, or $NR^6$ wherein $R^6$ is alkyl, aryl, arylkyl, or acyl.

A preferred class of compounds is represented by the general formula (2),

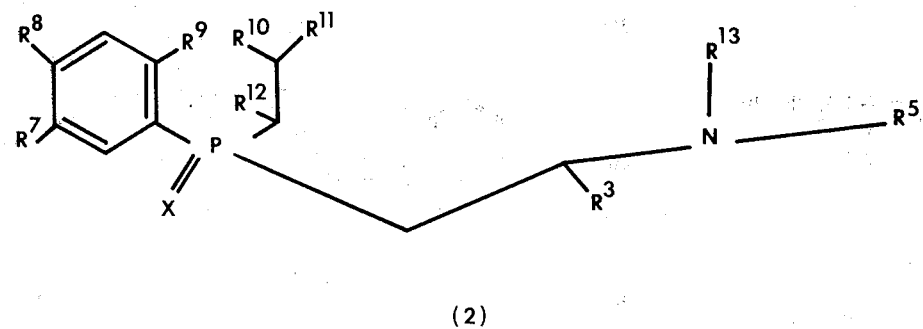

(2)

in which
- $R^3$ = H, or lower alkyl;
- $R^5$ = H, saturated or unsaturated alkyl, aralkyl, or may be bound to $R^{13}$, optionally through an oxygen atom, to form a ring;
- $R^7$ = H, hydroxyl, or alkoxyl;
- $R^8$ = H, hydroxyl, alkoxyl, or alkyl;
- $R^9$ = H, or $R^9$ and $R^{10}$ together may represent a single bond or a methylene bridge;
- $R^{10}$ = H, alkyl, or $R^9$ and $R^{10}$ together may represent a single bond or a methylene bridge;
- $R^{11}$ = H, or $R^{13}$ and $R^{11}$ together may represent a single bond;
- $R^{12}$ = H or lower alkyl;
- $R^{13}$ = methyl, or $R^{13}$ and $R^{11}$ together may represent a single bond;
- X = lone pair of electrons, O, S, or $NR^6$, wherein $R^6$ is alkyl, aryl, aralkyl, or acyl.

The compounds 3 to 27 inclusive shown herein below, are especially preferred:

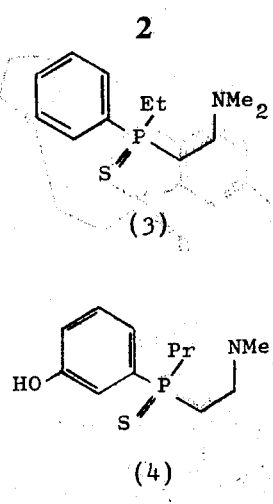

(3)

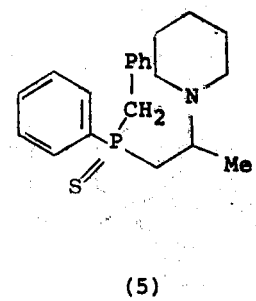

(4)

(5)

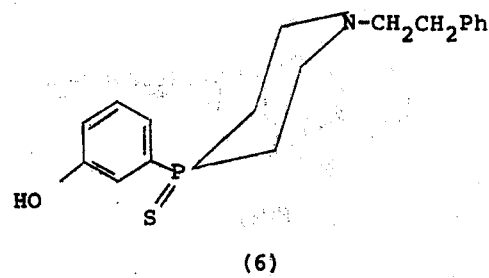

(6)

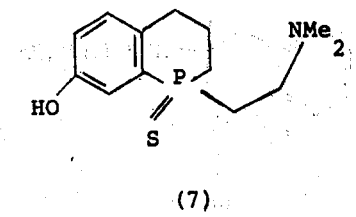

(7)

3
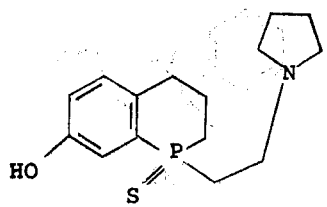
(8)
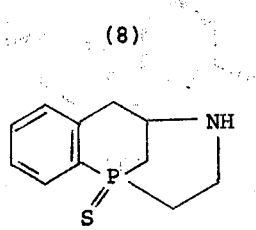
(9)
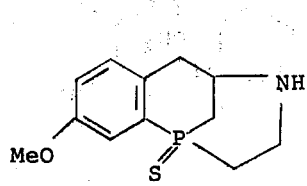
(10)
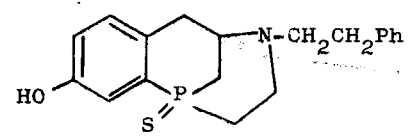
(11)
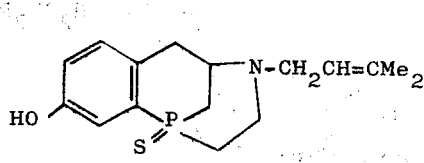
(12)
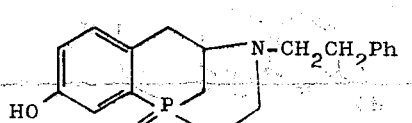
(13)
4
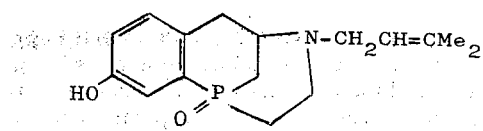
(14)
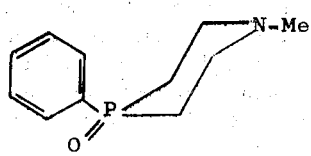
(15)
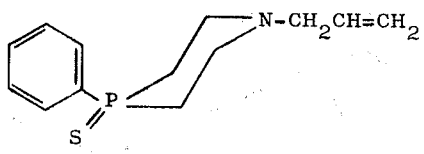
(16)
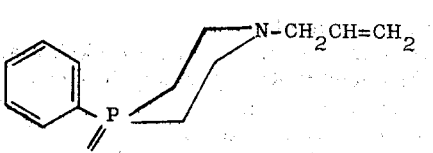
(17)
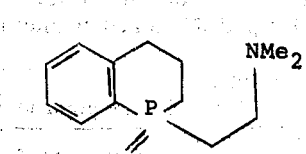
(18)
(19)

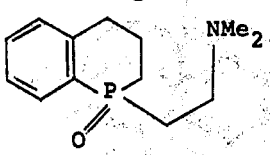

(20)

(25)

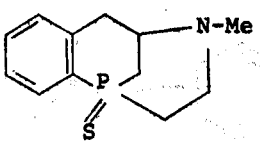

(21)

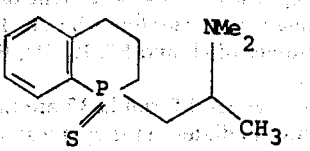

(26)

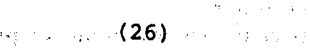

(22)

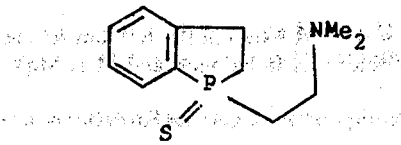

(27)

Another preferred class of compounds is represented by formula (1), where $R^1$ and $R^2$ (which may be the same or different) are preferably chosen from phenyl, p-chlorophenyl, hydroxyphenyl, or tolyl;

$R^3$ = methyl;

$R^4$ and $R^5$, which may be the same or different, are preferably chosen from lower alkyl groups, or together may form a heterocycle which is preferably pyrrolidine, piperidine, or morpholine.

The compounds 28 to 31 inclusive shown herein below are especially preferred:

(23)

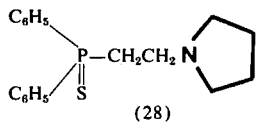

(28)

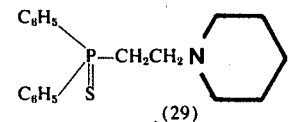

(29)

(24)

(30)

(31)

We also provide a method of manufacture of compounds of general formula 1 which method comprises reacting a compound of general formula 32

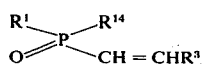 (32)

with an amine of general formula (33)

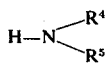 (33)

and optionally treatment with trichlorosilane optionally followed by treatment with sulphur wherein $R^{14}$ is either $R^2$ or unsaturated alkyl, and $R^2$, $R^3$, $R^4$, $R^5$ are as defined hereinbefore.

The compounds of general formula 32 are new compounds of use as intermediates in the synthesis of useful organo phosphorus compounds. These compounds form part of our invention.

In a further aspect of our invention we provide a method of manufacture of the compounds of general formula 32 which method comprises treating a compound of general formula 34

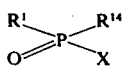 (34)

with $R^3 - CH = CH - M$ wherein $R^1$, $R^{14}$ and $R^3$ are as defined hereinbefore, X is halogen and M is MgX, Na or Li.

Certain of the compounds of general formula 34 are novel and in a further aspect of our invention we provide a process for the manufacture of

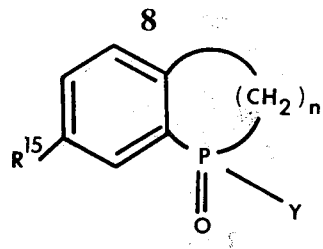

wherein n is 2 or 3 and Y is hydroxy or a halogen, $R^{15}$ is hydrogen or alkyl, which process comprises treating

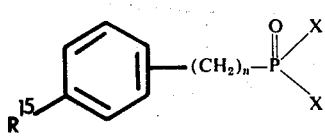

wherein X is halogen, successively with zinc chloride, acid hydrolysis hydrogen peroxide and optionally with a halogenating agent.

Thus for example, the 4 azaphosphorines may be prepared by reacting an amine $RNH_2$, with an aryldivinylphosphine oxide. For example, the reaction of divinylphosphine oxide with aqueous methylamine under reflux for 30 min gave a quantitative yield of 1-methyl-4-oxo-4-phenylperhydro-1,4-azaphosphorine (16), which was converted into the corresponding sulphide (17) by successive treatment with trichlorosilane, and sulphur.

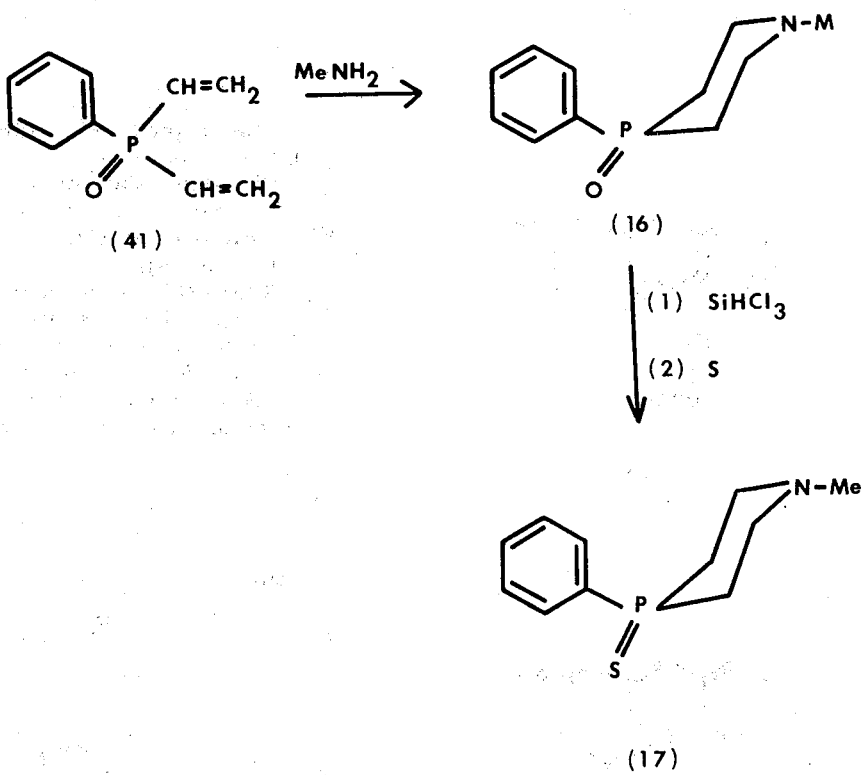

Compound (28) and related compounds may be, for example, prepared by reacting the corresponding amine (i.e. pyrrolidine, piperidine, or morpholine) with diphenylvinylphosphine sulphide:

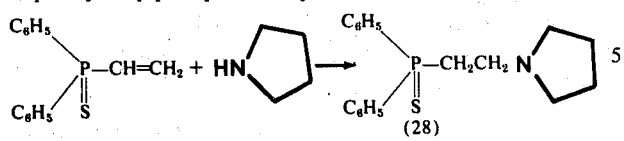

(28)

The synthesis of the bicyclic and tricyclic compounds is illustrated by the preparation of 19 and 21, Flowsheet 1. The procedure constitutes a new convenient synthesis of 1, 2,3,4-tetrahydrophosphinolines and phosphindolines, and of the corresponding dehydro derivatives, and is useful in the synthesis of condensed ring systems containing these entities.

FLOWSHEET 1

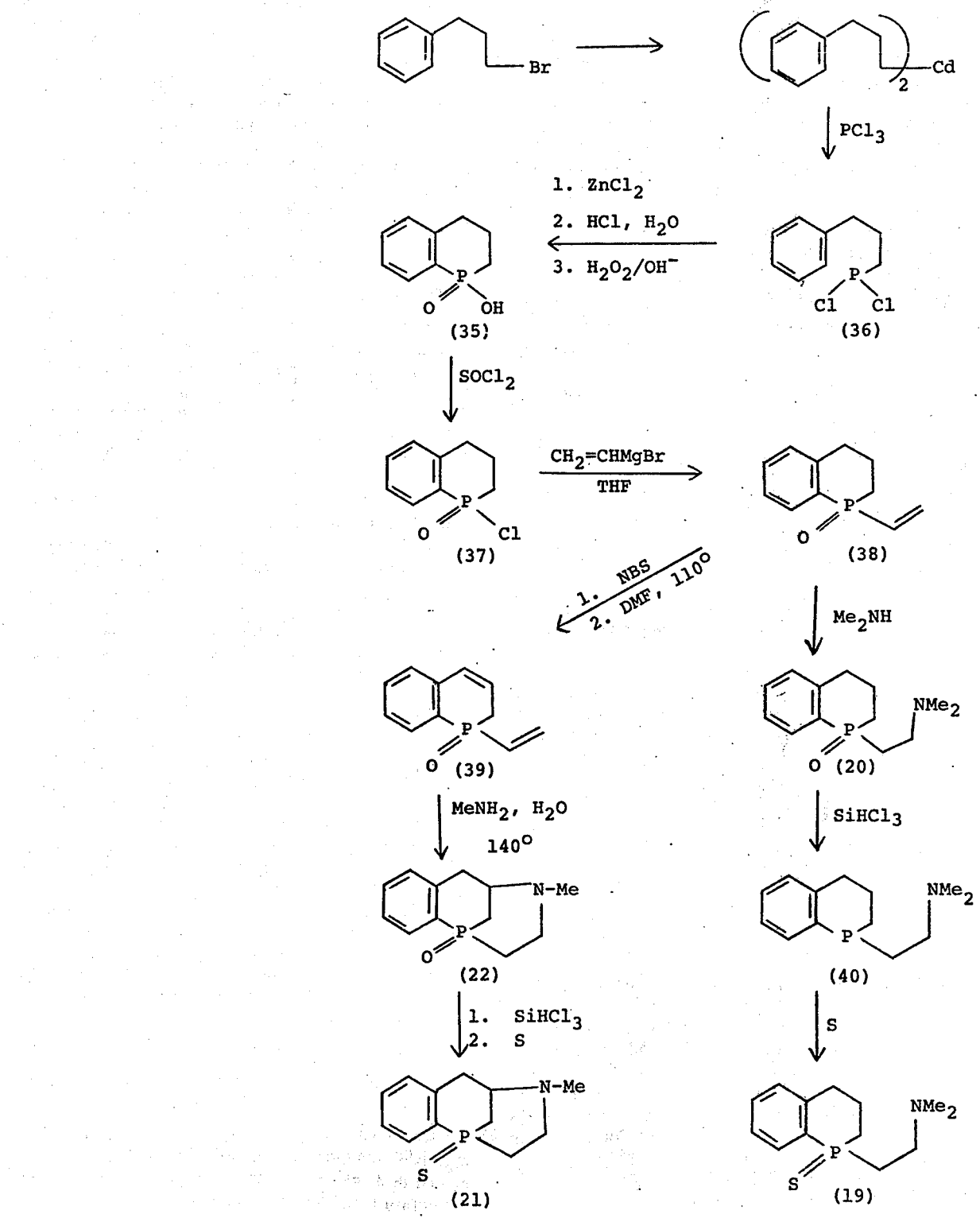

The new compounds 41, 42, 35, 36, 38 and 39 are of particular value as intermediates in the synthesis of organo phosphorus compounds.

Experimental procedures are exemplified below in the preparation of compounds 16, 17, 19, 21, 28, 29 and 30.

Biological Assay

The compounds described above were subjected to a Mouse Writhing Test and to the McKenzie Beechey Mouse Tail Stimulation Test (1962, Archives Internationales de Pharmacodynamae et de Therapie, 135) to determine their analgesic activities. The test compounds were prepared as 1.0% solutions in carboxymethylcellulose. The control in all tests was carboxymethylcellulose.

High activity was shown by compounds in which X = S. For example, compound (19) was active at 16mg/kg in the Tail Stimulation Test, comparable to morphine in this assay, and in the toxicity test showed $L_n$ 50, 170 mg/kg.

EXAMPLE 1

3-Phenylpropylphosphonous dichloride (36)

Anhydrous cadmium chloride (44g, 0.24 mole) was added rapidly to a stirred solution of 3-phenylpropyl magnesium bromide which had been prepared from magnesium (11.0g, 0.47 mole) and 3-phenylpropyl bromide (93g, 0.46 mole) in dry ether (500 ml).

Following the addition, the mixture was stirred in an ice bath for 2 hr. This reaction mixture, including the precipitate, was added slowly over 25 min to a vigorously stirred solution of phosphorus trichloride (100g, 0.73 mole) in dry ether (100 ml) kept below −20° with a dry ice-acetone bath. After the addition the reaction vessel was allowed to warm to room temperature, then heated at reflux for 2.5 hr. The cooled mixture was filtered through a sintered glass funnel and the white precipitate was washed several times with ether. Evaporation of the filtrate and washings, and distillation of the residue through an 18 inch spinning band column gave, as the major fraction, 3-phenylpropyl phosphonous dichloride, b.p. 78°/0.2 mm, a colourless liquid. This was purified by distillation through a 9 inch Vigreux column (50g, 49%). (Found: C, 48.6; H, 5.0; P, 14.2 $C_9H_{11}PCl_2$ requires C, 48.9; H, 5.0; P, 14.0%). $\nu_{max}$: 3070, 3050, 3020, 2920, 2850, 1600, 1490, 1450, 1070, 1030, 750, 710 cm$^{-1}$. N.m.r. spectrum (CCl$_4$): 7.19, m. 5H (aromatic); 2.68, distorted t, 2H (benzylic); 1.7–2.7, m, 4H(methylenes). Mass spectrum: m/e 221 (1.4%), 118 (10 ), 102 (10), 92 (100), 78 (12.5), 66 (38), 52(21).

EXAMPLE 2

1-Hydroxy-1-oxo-1,2,3,4-tetrahydrophosphinoline (35)

3-Phenylpropylphosphonous dichloride (60g, 0.27 mole) was heated at 170° with freshly fused, powdered zinc chloride (60g, 0.44 mole) for 6 hr with rapid stirring. The mixture was then cooled to 150°, and concentrated hydrochloric acid (100 ml) was added cautiously with rapid stirring. The mixture was heated under reflux for a further 15 min, then the excess of acid was removed in vacuum. The oily residue was taken up in aqueous potassium hydroxide (250 ml, 10%), and hydrogen peroxide (50 ml, 30%) was added. The mixture was stirred at room temperature for 24 hr, acidified, and extracted with chloroform. The chloroform solution was washed with distilled water, then extracted 3 times with potassium hydroxide solution (10%). The combined alkali extract was washed with chloroform, then acidified, and re-extracted with chloroform to give colourless crystals (20g, 41%), m.p. 140°–4°. Crystallization from ethanol gave 1-hydroxy-1-oxo-1,2,3,4-tetrahydrophosphinoline, m.p. 146–147 (Found: C, 59.3; H, 5.7; P, 17.2. $C_9H_{11}PO_2$ requires C, 59.3; H, 6.1; P, 17.0%). Infrared spectrum $\nu_{max}$: 2600, 2280, 1600, 1320, 1230, 1180, 1165, 1150, 1100, 1030, 980, 970, 800, 785 cm$^{-1}$. N.m.r. spectrum (CDCl$_3$): 12.5, s, 1H (OH); 6.8 – 8.2, m, 4H (aromatic); 2.8 – 3.4, m, 2H (benzylic); 1.9 – 2.8, m, 4H (methylenes). Mass spectrum: molecular ion, m/e 182.

Evaporation of the original chloroform extract, gave colourless crystals (28g). The n.m.r. spectrum of this material indicated the presence of some of the secondary phosphine oxide, 1-oxo-1,2,3,4-tetrahydrophosphinoline. This mixture was again treated with alkaline hydrogen peroxide, and a similar work-up gave a further 25g of crystalline 1-hydroxy-1-oxo-1,2,3,4-tetrahydrophosphinoline, m.p. 142°–4°.

EXAMPLE 3

1-Oxo-1-vinyl-1,2,3,4-tetrahydrophosphinoline (38)

1-Hydroxy-1-oxo-1,2,3,4-tetrahydrophosphinoline (2.7g, 15 mmole) was refluxed with redistilled thionyl chloride (12 ml, 170 mmole) for 2 hr, and the excess of thionyl chloride removed by distillation. Distillation of the residue (bulb to bulb) at 150°/0.005 mm gave 1-chloro-1-oxo-1,2,3,4-tetrahydrophosphinoline (34), a light yellow fuming solid (2.3g, 76%). This was used without further purification.

To a rapidly stirred solution of the above phosphinic chloride (4g, 20 mmole) in dry tetrahydrofuran (25 ml) cooled in a dry ice-acetone bath was added a tetrahydrofuran solution of vinyl magnesium bromide (20 ml of 1M, 20 mmole) at a rate of 1 ml/min. This was introduced directly into the solution using a syringe in order to prevent crystallization of the Grignard reagent on the sides of the cooled vessel. Following the addition, the solution was stirred for a further 30 min at −70°, then treated with saturated ammonium chloride solution. The mixture was extracted with chloroform, washed with sodium hydroxide (10%), then with distilled water, dried and evaporated. Distillation of the residue (bulb to bulb) at 130°/0.001 mm gave pure 1-oxo-1-vinyl-1,2,3,4-tetrahydrophosphinoline as colourless hygroscopic crystals (2.9g, 74%). (Found: C, 68.4; H, 6.8; P, 15.5. $C_{11}H_{13}PO$ requires: C, 68.7; H, 6.8; P, 16.1%). Infrared spectrum $\nu_{max}$: 2950, 1600, 1490, 1450, 1320, 1200, 1150, 1100, 1000, 940, 840, 800, 770, 740 cm$^{-1}$. N.m.r. spectrum (CDCl$_3$): 7.0–8.0, m, 4H (aromatic); 5.6–6.6, m, 3H (olefinic); 2.6 – 3.1, m, 2H (benzylic); 1.7 – 2.5, m, 4H (methylenes). Mass spectrum: m/e 192 (100%), 191 (53), 165 (33), 164 (94), 149 (28), 147 (30), 133 (25), 117 (42), 116 (25), 115 (50), 91 (20); m* 140 (192–164).

EXAMPLE 4

1-(2-N,N-Dimethylamino)ethyl-1-oxo-1,2,3,4-tetrahydrophosphinoline (20).

1-Oxo-1-vinyl-1,2,3,4-tetrahydrophosphinoline (300 mg, 1.56 mmole) and dimethylamine (15 ml) were placed in a sealed tube and allowed to stand at room temperature for 24 hr. Evaporation of the excess of dimethylamine gave a light yellow oil. Gas chromatography showed one product together with a very small amount of starting material. Distillation (bulb to bulb) at 140°/0.001 mm gave a colourless hygroscopic oil. An analytical sample was purified by preparative t.l.c. on silica gel plates developed with chloroform-methanol 5-1, followed by bulb to bulb distillation. Complete removal of water was very difficult (Found: C, 65.2; H, 8.8; N, 5.5; $C_{13}H_{20}NOP$ requires C, 65.8; H, 8.5; N, 5.9%). Infrared spectrum $\nu_{max}$: 2940, 2870, 2830, 2780, 1615, 1595, 1460, 1440, 1300, 1265, 1175, 1080, 1050, 850, 825, 760 $cm^{-1}$. N.m.r. spectrum ($CDCl_3$): 7.0–8.1, m, 4H (aromatic); 1.6–3.0, m with a sharp singlet at 2.20, 16H (aliphatic). Mass spectrum 237 (5%), 164 (11), 72 (97), 71 (100), 58 (31), 56 (10).

The perchlorate, m.p. 216°–217° from ethanol, was not hygroscopic (Found: C, 46.1; H, 6.3; N, 4.0; Cl, 10.5. $C_{13}H_{21}ClNO_5P$ requires C, 46.4; H, 6.3; N, 4.2; CL, 10.5%).

EXAMPLE 5

1-(2-N,N-Dimethylamino)ethyl-1-thio-1,2,3,4-tetrahydrophosphinoline (19)

A solution of 1-(2-N,N-dimethylamino) ethyl-1-oxo-1,2,3,4-tetrahydrophosphinoline (4.0g, 15.7 mmole) (hydrated form) in benzene (50 ml) was dried by azeotropic distillation, then cooled to room temperature and placed under a nitrogen atmosphere. Whilst the solution was being stirred, trichlorosilane (4 ml, 40 mmole) was added, then the mixture was heated under reflux for 2 hr. The reaction mixture was evaporated to half of its original volume to remove the excess of trichlorosilane, then sulphur (3g) was added and the mixture was stirred at room temperature for 12 hr. The benzene solution was washed with sodium hydroxide solution (2M), then the product was extracted into hydrochloric acid (2M). The combined acid extract was washed with benzene, made alkaline with sodium hydroxide solution (5M) and the basic material was extracted into chloroform. The chloroform extract was washed with saturated ammonium chloride, dried ($Na_2SO_4$) and evaporated. Bulb to bulb distillation of the residue at 150°/0.005 mm yielded a light cream oil (3.8g, 95%), which slowly crystallized, m.p. 58°–60°. G.l.c. (B) showed a single peak, but t.l.c. showed some minor impurities. These were removed by preparative t.l.c. (chloroform methanol, 15:1), redistillation of the residue as above gave a light yellow oil which slowly crystallized (Found: C, 61.7; H, 8.1; P, 12.1; S, 13.3. $C_{13}H_{20}NPS$ requires C, 61.7; H, 8.1; P, 12.2; S, 12.7%). Mol. wt. (mass spectrum), 253.$\nu_{max}$(film): 2960, 2940, 2860, 2820, 2770, ($N-CH_3$ and $N-CH_2-$), 1465, 1440 ($C_6H_5-P$), 1265, 1160, 1135, 1080, 1050, 1015, 860, 780, 750, 725, 695, and 660 $cm^{-1}$. $\lambda_{max}$: 216 (9000), 250 nm (2530). N.m.r. spectrum ($CDCl_3$) 7.93, dm, 1H (H8); 7.0–7.6, m, 3H (H5, H6 and H7); 1.7–3.2, m with a sharp singlet at 2.20, 16H (aliphatic protons).

The hydrochloride salt separated from absolute ethanol as colourless crystals, m.p. 238°–241° (Found: C, 53.6; H, 7.4; P, 10.5; S, 11.1. $C_{13}H_{21}ClNPS$ requires C, 53.9; H, 7.4; P, 10.5; S, 10.9%).

EXAMPLE 6

1-Oxo-1-vinyl-1,2-dihydrophosphinoline (39)

To a hot solution of 1-oxo-1-vinyl-1,2,3,4-tetrahydrophosphinoline (4g, 2.04 mmole) in chloroform (30 ml) was added N-bromosuccinimide (4.4g, 2.7 mmole), and the boiling mixture was irradiated with a 300 watt sun lamp until the brown colour had disappeared. Evaporation of the washed, dried solution gave a cream oil (5.5g). N.m.r. spectrum ($CDCl_3$): 6.8–7.7, m, 4H(aromatic); 5.4–6.5, m, 3H(olefinic); 5.1–5.4, bd, 1H (bromobenzylic); 1.8–2.8, m, 4H (methylenes). This crude material was used directly for the next step.

A solution of the crude 4-bromo-1-oxo-1-vinyl-1,2,3,4-tetrahydrophosphinoline (5.5g) in anhydrous dimethyl formamide (30 ml) was heated under nitrogen at 110° for 45 min, after which time an n.m.r. spectrum indicated that dehydrobromination was complete. The excess of dimethyl formamide was evaporated in vacuum, and the brown semi-solid residue was dissolved in chloroform. This solution was washed with water, dried, and evaporated. Distillation of the residue through a short Vigreux column gave a colourless liquid b.p. 134°–138°/0.005 (3.6g, 90%). Preparative t.l.c. on silica gel plates developed with chloroform-methanol 30–1, followed by bulb-to-bulb distillation gave the "pure" compound. However, complete removal of water was not achieved, nor was a unique hydrate obtained, and the compound failed to give satisfactory microanalytical figures. Infrared spectrum $\nu_{max}$: 3030, 2930, 2860, 1630, 1590, 1475, 1440, 1390, 1275, 1180, 1140, 990, 865, 785, 720 $cm^{-1}$. N.m.r. spectrum ($CDCl_3$): 7.0–8.0, m. 4H (aromatic); 5.6–6.8, m, 5H (olefinic); 2.6–3.1, m, 2H (methylene). Mass spectrum: m/e 190 (57%), 141 (41), 128 (38), 116 (66), 115 (100), 89 (27), 65 (34), 51 (50). Ultraviolet spectrum $\lambda_{max}$ (ethanol): 222 (19600) 262 (4200), 298 (2300).

EXAMPLE 7

2-Methyl-5-oxo-5-phosphabenzomorphan (22)

A solution of 1-oxo-1-vinyl-1,2-dihydrophosphinoline (0.25g, 1.3 mmole) in aqueous methylamine (3 ml of 0.5M = 1.5 mmole) was heated at 140° in a sealed tube 48 hr. The cooled solution was treated with saturated ammonium chloride and extracted with chloroform. Evaporation of the dried extract gave an orange oil (300 mg). Bulb to bulb distillation at 160°/0.005 mm gave colourless hygroscopic crystals (0.22g, 77%), m.p. 121°–122°. Infrared spectrum: $\nu_{max}$ (Nujol): 2905, 2895 ($N-CH_2$), 1595, 1410, 1400, 1380, 1315, 1290, 1280, 1260, 1235, 1190 (P=O), 1170, 1150, 1145, 1115, 1090, 1070, 1035, 990, 980, 955, 950, 910, 840, 820, 775, 760, 735, 715, 695, and 665 $cm^{-1}$. Ultraviolet spectrum: $\lambda_{max}$ 213 (8370), 270 (812), 277 nm (800). N.m.r. spectrum ($CDCl_3$): δ7.91, dm, 1H (o-aromatic); 7.1–7.5, m, 3H (aromatic); 3.68, bd, 1H (bridgehead H); 3.0–3.28, m, 2H (benzylic); 1.4–2.9, m, with a sharp peak at 2.47, 9H (N-Me and methylenes). Mass spectrum: molecular ion m/e 221.

The hydrochloride salt, crystallised from anhydrous ethanol had mp >250° dec. (Found: C, 56.4; H, 6.7; N, 5.6; P, 11.8. $C_{12}H_{17}ClNOP$ requires C, 56.0; H, 6.6; N, 5.4; P, 12.0%).

EXAMPLE 8

The Tricyclic Phosphine Sulphide (21)

A solution of 4-methyl-1,2,3,4,5,6-hexahydro-1,5-methano-4,1-benzazaphosphorine-1-oxide (5.5g, 24.8 mmole) in benzene (100 ml) was dried by azeotropic distillation, then cooled to room temperature and placed under a nitrogen atmosphere. Whilst the solution was being stirred, trichlorosilane (5 ml, 50 mmol) was added and the mixture was heated under reflux for 2 hr. After evaporation to half volume to remove the excess of trichlorosilane, sulphur (4g) was added, and the mixture stirred at room temperature for 12 hr. The benzene solution was washed with sodium hydroxide solution (2M), saturated ammonium chloride, water and then dried ($Na_2SO_4$). Passage of dry hydrogen chloride through this gave the hydrochloride which was collected, and stirred in refluxing benzene for 2 hr to remove sulphur; filtration of the cooled suspension gave a white solid. This procedure was repeated to remove the last traces of sulphur. Crystallization from absolute ethanol afforded the hydrochloride of compound (21). (5.6g, 82%), m.p. 252°–253° (Found: C, 52.4; H, 6.4; P, 11.2; N, 4.9. $C_{12}H_{17}ClNPS$ requires C, 52.7; H, 6.3; P, 11.3; N, 5.1%). The free base, recovered in the usual way, was recrystallized from cyclohexane/benzene (3:1) to give compound (21) as colourless crystals, m.p. 137°–138° (Found: C, 60.5; H, 6.8; N, 5.7; P, 13.0. $C_{12}H_{16}NPS$ requires, C, 60.7; H, 6.8; N, 5.9; P, 13.0%). $\nu_{max}$ (Nujol): 2810 (N—$CH_2$ or N—$CH_3$), 2785, 1445 ($C_6H_5$-P), 1430, 1400, 1380, 1300, 1270, 1225, 1180, 1120, 1085, 1070, 995, 990, 955, 875, 770, 755, 735, 710, 705 cm$^{-1}$. P.m.r. (100 MHz) ($CDCl_3$): 8.05, dm, $J_{P-H}$ = 15.2, 1H (aromatic, ortho to P); 7.1 – 7.5, m, 3H (aromatic, meta and para to P); 3.58, dm, $J_{P-H}$ = 26, 1H (bridgehead proton), 1.5–3.5, m, with a sharp singlet, at $\delta$2.46, 11H (N-$CH_3$ and 4 × $CH_2$). Mass spectrum: 237, parent ion. $\lambda_{max}(\epsilon)$: 210 (9880), 268 (520), 276 nm (460).

EXAMPLE 9

1-Methyl-4-oxo-4-phenylperhydro-1,4-azaphosphorine (16)

A mixture of divinylphenylphosphine oxide (0.40g, 2.24 mmol) and aqueous methylamine (2.6 ml of 1M = 2.7 mmol) was heated under reflux for 30 min. The aqueous solution was cooled, saturated with ammonium chloride, and extracted with chloroform. Bulb to bulb distillation of the product at 140°/0.005 mm gave 1-methyl-4-oxo-4-phenylperhydro-1,4-azaphosphorine (0.46g, 98%), as colourless hydroscopic crystals, m.p. 115°–116°. The m.p. was not raised by recrystallization from anhydrous benzene, cyclohexane (1:3). The purity of this material was confirmed by t.l.c. (chloroform-methanol (3:1)). A freshly dried sample (80°/5 mm over $P_2O_5$) gave slightly low carbon and phosphorus values owing to rapid uptake of water prior to analysis (Found: C, 62.6; H, 7.8; P, 14.6. $C_{11}H_{16}NOP$ requires C, 63.2; H, 7.7; P, 14.8%). Mol. wt. (Mass spectrum), 209. Infrared spectrum $\nu_{max}$ (Nujol): 2820 (N—$CH_2$), 1590, 1460 ($C_6H_5$—P), 1410, 1380, 1320, 1265, 1170, (P=O), 1110, 1065, 990, 960, 925, 810, 760, 725, 705, 665 cm$^{-1}$. N.m.r. spectrum ($CDCl_3$): 7.82, dm, 2H (o-aromatic); 7.4–7.7, m, 3H (m- and p-aromatic); 2.6–3.3, m, 4H (methylenes); 2.36, s, 3H (methyl); 1.8–2.5, m, 4H (methylenes). A sample which had been exposed to the atmosphere for a few min showed additional broad absorption bands at 3400 and 1630 cm$^{-1}$ in the i.r. spectrum, and additional sharp singlets at $\delta$3.06 and 4.62 (exchanged by $D_2O$) in the n.m.r. spectrum.

EXAMPLE 10

1-Methyl-4-phenyl-4-thioperhydro-1,4-azaphosphorine (15)

1-Methyl-4-oxo-4-phenylperhydro-1,4-azaphosphorine (4.0g, 19.1 mmol) was reduced with trichlorosilane (4 ml, 40 mmol) in benzene solution, and the crude phosphine treated with sulphur (2g) at room temperature for 12 hr. The product was treated with dry hydrogen chloride in the usual way to give 1-methyl-4-phenyl-4-thioperhydro-1,4-azaphosphorine hydrochloride (4,1g, 82%), m.p. 233°–235° (Found: C, 50.2; H, 6.6; P, 11.7; S, 11.9. $C_{11}H_{17}ClNPS$ requires C, 50.5; H, 6.6; P, 11.8; S, 12.3%). The free base was regenerated from the hydrochloride and distilled (bulb to bulb) at 160°/0.005 mm. Crystallization from cyclohexane/hexane (1:1) gave colourless crystals, m.p. 103°–104° (Found: C, 58.2; H. 7.1; P, 13.5; S, 14.1. $C_{11}H_{16}NPS$ requires C, 58.7; H, 7.2; P, 13.7; S, 14.2%). $\nu_{max}$ (Nujol): 2820 (N—$CH_2$), 1450 ($C_6H_5$—P), 1435, 1400, 1380, 1265, 1255, 1190, 1125, 1115, 1070, 1035, 1030, 990, 965, 930, 800, 755, 725, 715 and 695 cm$^{-1}$. N.m.r. spectrum ($CDCl_3$): 7.94, dm, 2H (o-aromatics); 7.4–7.6, m, 3H (m- and p-aromatics); 1.6–3.3, m with a sharp singlet at 2.42, 11 (n-Me and methylenes).

EXAMPLE 11

2-Pyrrolidinoethyldiphenylphosphine sulphide (28)
(N-Me

Reaction of diphenylvinylphosphine sulphide with pyrrolidine, and distillation of the product at approximately 170°/0.2 mm gave a pale yellow oil which was dissolved in ether and treated with anhydrous hydrogen bromide. Crystallisation from ethanol gave the hydrobromide (32) of the amine (28) as white plates, m.p. 247° (61%). (Found: C, 54.3; H, 5.8; Br, 20.3. $C_{18}H_{23}BrNPS$ requires C, 54.6; H, 5.6; Br, 20.2%).

The amine (28) showed the following properties: Mass spectrum: molecular ion at m/e 315. N.m.r. ($CDCl_3$): 7.4–8.2, m, 10H (aromatic); 2.7–3.6, m, 4H (methylene); 2.3–2.7, m, 4H (methylene); 1.5–2.0, m, 4H (methylene). Infrared spectrum ($\nu_{max}$): 3060, 2940, 2500, 1635, 1440, 1180, 1105, 1025, 995, 975, 875, 735, 710, 690 cm$^{-1}$.

EXAMPLE 12

2-Piperidinoethyldiphenylphosphine sulphide (29)

The hydrobromide (33) of the amine (29) was obtained as white plates, m.p. 214° (60%). (Found: C, 55.7; H, 6.0; Br, 19.8. $C_{19}H_{25}BrNPS$ requires C, 55.6; H, 6.1; Br, 19.5%).

The amine (29) showed the following properties: Mass spectrum: molecular ion m/e 329. N.m.r. spectra ($CDCl_3$): 7.3–8.2, m, 10H (aromatic); 1.6–1.9, m, (methylene); 2.4–2.6, m, 4H (methylene); 1.2–1.6, m, 6H (methylene). Infrared spectrum ($\nu_{max}$): 3060, 2950, 2830, 1425, 1355, 1305, 1180, 1100, 1070, 1030, 1000, 975, 830, 800, 745 cm$^{-1}$.

EXAMPLE 13

2-Morpholinoethyldiphenylphosphine sulphide (30)

The hydrobromide (34) of the amine (30) was obtained as white needles, m.p. 212° (69%).

The amine (30) showed the following properties: Mass spectrum: molecular ion m/e 331. N.m.r. spectrum (CDCl$_3$): 7.4–8.7, m, 10H (aromatic); 2.7–3.6, m, 4H (methylene); 2.3–2.7, m, 4H (methylene); 1.5–2.0, m, 4H (methylene). Infrared spectrum ($\nu_{max}$): 3080, 2950, 2880, 2840, 1440, 1360, 1310, 1275, 1150, 1110, 1070, 1030, 1000, 975, 910, 860, 810, 745, 690 cm$^{-1}$.

EXAMPLE 14

2-Phenylethylphosphonous dichloride

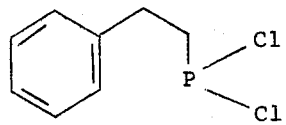

This compound was prepared from 2-phenylethylbromide (230g, 1.24 mole) by the method described above for the preparation of 3-phenylpropylphosphonous dichloride. 2-Phenylethylphosphonous dichloride was obtained as a pungent colourless liquid (115g, 45%), b.p. 64–66 at 0.001 mm.

EXAMPLE 15

1-Hydroxyphosphindoline 1-oxide

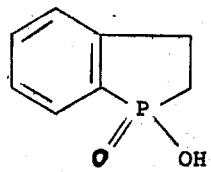

This compound was prepared from 2-phenylethylphosphonous dichloride (50g, 0.24 mol) by the same method as for the preparation of 1-hydroxy-1,2,3,4-tetrahydrophosphinoline 1-oxide described above. The crude material was obtained as colourless crystals (31g, 72%), m.p. 141°–142°. Crystallisation from cyclohexane/benzene followed by sublimation at 135°/0.001 mm gave a pure sample of 1-hydroxyphosphindoline-1-oxide, m.p. 144°–145°.

EXAMPLE 15A

1-Methoxyphosphindoline 1-oxide

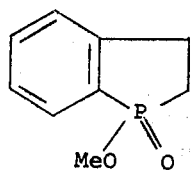

Esterification of a sample of crude 1-hydroxyphosphindoline 1-oxide (1.0g, 5.0 mmol) with diazomethane by the same method as for the preparation of 1-methoxy-1,2,3,4-tetrahydrophosphinoline 1-oxide described above, and the product was purified by bulb to bulb distillation at 120°/0.01 mm (1.1g, 98%). This material was shown to be essentially homogeneous by g.l.c. and the p.m.r. spectrum which showed only one set of doublets, 3.71, attributable to a <=POCH$_3$ group.

EXAMPLE 16

1-Ethylphosphindole 1-oxide

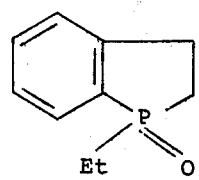

This compound was prepared from 1-hydroxy-phosphindoline 1-oxide (3.0g, 17.9 mmol) by a method similar to that used for the preparation of 1-ethyl-1,2,3,4-tetrahydrophosphinoline 1-oxide described above, except that anhydrous tetrahydrofuran was used as solvent. Isolation with chloroform and bulb to bulb distillation of the residue at 160°/0,1 mm gave a colourless hygroscopic liquid (2.3 g, 72%). Preparative T.l.c. (R$_F$0.38, chloroform/methanol 15:1), and bulb to bulb distillation of the major component gave "pure" 1-ethylphosphindoline-1-oxide as a colourless hygroscopic liquid. This was shown to be pure by g.l.c.

EXAMPLE 17

1-Vinylphosphindoline 1-oxide

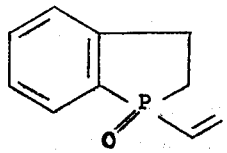

This was prepared from 1-hydroxy phosphindole 1-oxide (19.0g, 0.113 mol) using a method analogous to that described for the preparation of 1-vinyl-1,2,3,4-tetrahydrophosphinoline 1-oxide described above. The chloroform extract yielded a liquid which was distilled through a short Vigreux column to give a colourless hygroscopic liquid (14.9g, 74%), b.p. 116°–118°/0.01 mm. Attempted crystallization of this material from anhydrous cyclohexane/benzene gave a small amount of an extremely deliquescent crystalline solid which separated slowly over 4 days, m.p. 35°–36°, after prolonged drying over phosphorus pentoxide at 0.1 mm. Preparative T.l.c. of a portion of this (R$_F$0.18, chloroform/methanol 30:1) gave, after bulb to bulb distillation at 130°/0.01 mm, a pure sample of 1-vinylphosphindoline 1-oxide as a colourless hygroscopic liquid. This was shown to be pure by g.l.c.

EXAMPLE 18

1-(2-N,N-Dimethylaminoethyl)phosphindoline 1-oxide

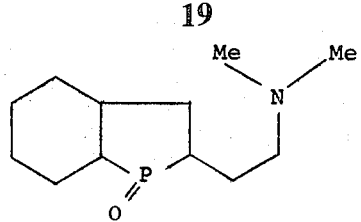

This compound was prepared by reaction of crude 1-vinylphosphinoline 1-oxide (5.0g, 28.1 mmol) with aqueous methylamine using the procedure described above for the preparation of 1-(2,N,N-dimethylaminoethyl)-1,2,3,4-tetrahydrophosphinoline 1-oxide. Extraction with chloroform and bulb to bulb distillation of the residue at 150°/0.005 mm gave a colourless hygroscopic liquid (5.83g, 93%).

T.l.c. (chloroform/methanol 3:1) indicated that this liquid contained a significant amount of an impurity (5–10%) which could not be removed by recrystallization of the derived hydrochloride or by chromatography of the free amine on an alumina column. A sample of the crude product was subjected to preparative T.l.c., followed by three successive bulb to bulb distillations to give pure 1-(2-N,N-dimethylaminoethyl)phosphindoline 1-oxide. The mass spectrum showed the molecular ion at m/l 223 (3%).

EXAMPLE 19

1-(2,N,N-Dimethylaminoethyl)phosphindoline 1-sulphide (27)

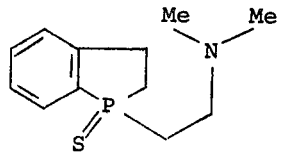

1-(2-N,N-Dimethylaminoethyl)phosphindoline 1-oxide (3.0g, 13.4 mmol) was reduced with trichlorosilane (3 ml, 30 mmol) and the phosphine oxidized with sulphur (3g). The hydrochloride salt of the product was obtained from absolute ethanol as colourless crystals (2.65g, 72%), m.p. 245°–246°. The free base was obtained from the hydrochloride in the usual way, and bulb to bulb distillation at 150°/0.005 mm afforded a pure sample of 1-(2-N,N-dimethylaminoethylphosphindoline 1-sulphide as a colourless liquid, the purity of which was confirmed by T.l.c. ($R_f$ 0.54 chloroform/methanol 15:1).

EXAMPLE 20

1-Methoxyphosphindole 1-oxide

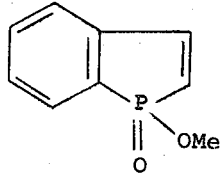

A solution of 1-methoxyphosphindoline 1-oxide (2.7g, 14.8 mmol) in carbon tetrachloride (50 ml) was stirred rapidly under irradiation with a 500 watt mercury arc lamp, and N-bromosuccinimide (2.9g, 16.3 mmol) was added cautiously in small portions during 10 min. The mixture was irradiated for an additional 10 min. then cooled and filtered to remove the precipitated succinimide. The filtrate was washed with water, dried ($Na_2SO_4$), and evaporated to give a colourless oil (3.5g) which gave a p.m.r. spectrum consistent with 3-bromo-1-methoxyphosphindoline 1-oxide. The crude bromo ester was dissolved in benzene (30 ml). Triethylamine was added and the solution heated under reflux with stirring for 3 min. The precipitated triethylamine hydrobromide was filtered off, the filtrate concentrated, and the residue distilled (bulb to bulb) at 140°/0.01 mm to give colourless deliquescent plates (2.0 g, 75). Recrystallization from carbon tetrachloride gave 1-methoxyphosphindole 1-oxide m.p. 89°–90°. The purity of this sample was confirmed by g.l.c. and T.l.c. ($R_f$ 0.53, chloroform/methanol 30:1).

EXAMPLE 21

1-Vinylphosphindole 1-oxide

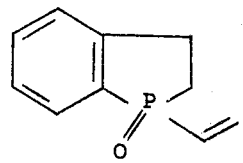

To a solution of 1-vinylphosphindoline 1-oxide (6.4g, 36.0 mmol) in carbon tetrachloride (80 ml) was added N-bromosuccinimide (6.8g, 38.6 mmol) and the two phase mixture stirred under reflux whilst being irradiated with a 500 watt mercury lamp. After 15 mins the solution was washed with water, the washings were extracted with chloroform and the combined organic extract was dried and evaporated to give a light yellow oil. A p.m.r. spectrum of this indicated that it was 3-bromo-1-vinylphosphindole 1-oxide. This material was heated under reflux with triethylamine (10 ml) for 5 mins, cooled, and the precipitated hydrobromide filtered off. The benzene filtrate was washed with water, dried and evaporated. Distillation gave an oil (5.8g, b.p. 170°/0.01 min), g.l.c. of which showed it to be about 90% pure.

EXAMPLE 22

4-Methyl-1,5-methano-2,3,4,5-tetrahydro-1H-4,1-benzazaphosphorine.

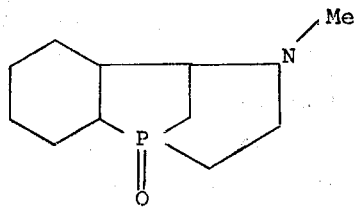

A solution of the above sample of 1-vinylphosphindole 1-oxide (1.5g, 8.5 mmol) in 0.5 m aqueous methylamine (10 ml, 10 mmol) was heated under reflux with stirring for 14 hr. The solution was then cooled and extracted with chloroform to give a cream oil (1.4g). The p.m.r. spectrum of this showed a small doublet of multiplets at 4.2 with major splitting of 28 Hz, attributable to the bridgehead benzylic proton.

To remove uncyclised secondary amine the above product was dissolved in aqueous sodium hydroxide solution (40 ml, 2M) and benzenesulphonyl chloride (3 ml) was added during 10 min. The mixture was heated on the water bath for 10 min, then cooled and the remaining basic material was isolated by extraction into hydrochloric acid (4 M). Basification of these extracts and isolation with chloroform gave the required product as an oil (1.1g).

EXAMPLE 23

1-(2,Pyrrolidinoethyl)-1-oxo-1,2,3,4-tetrahydro-phosphinoline.

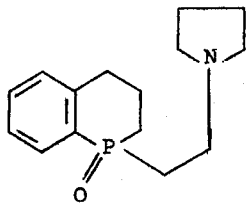

1-oxo-1-vinyl-1,2,3,4-tetrahydrophosphinoline (1g) was dissolved in pyrrolidine (2ml). After 24 hr. at room temperature the excess pyrrolidine was removed under reduced pressure and the residue purified by preparative T.l.c. The produce (0.7 g) was obtained as a colourless oil.

EXAMPLE 24

1-(2-Pyrrolidinoethyl)-1-thio-1,2,3,4-tetrahydro-phosphinoline

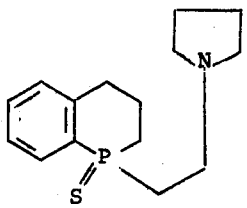

Trichlorosilane (2ml) was added to a solution of 1-oxo-1-(2-pyrrolidinoethyl)-1,2,3,4-tetrahydrophosphinoline (1.8g) in benzene (50 ml), and the mixture heated under reflux for 2 hr. Half the benzene was distilled off. Sulphur (1.5g) was added and the mixture stirred at room temperature for 12 hr. The mixture was then washed with 2M sodium hydroxide and the bases extracted into 2M hydrochloric acid. The acid extracts were washed with benzene, basified with 5M sodium hydroxide and extracted with chloroform. The residue after evaporation of the chloroform was purified by T.l.c. to give the phosphine sulphide as a pale yellow hygroscopic gum (1.5g).

EXAMPLE 25

1-(2-Piperidinoethyl)-1-thio-1,2,3,4-tetrahydro-phosphinoline

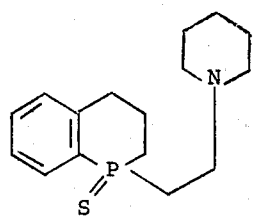

A procedure similar to that described above but using piperidine instead of pyrrolidine gave 1-(2-piperidinoethyl)-1-thio-1,2,3,4-tetrahydrophosphinoline as a colourless gum.

I claim:

1. A compound of the formula

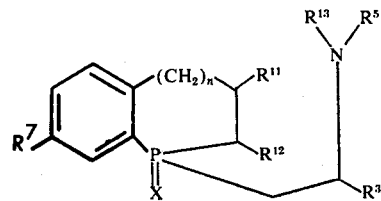

wherein $n$ is 0 or 1; X is O or S; $R^3$ is hydrogen or methyl; $R^5$ is hydrogen or methyl, or may be bound to $R^{13}$ to form a morpholino, piperidino or pyrrolidino ring; $R^7$ is hydrogen or hydroxy; $R^{11}$ and $R^{12}$ are hydrogen; $R^{13}$ is methyl, or $R^{13}$ and $R^5$ may be joined together as above stated to form a morpholino, piperidino, or pyrrolidino ring.

2. The compound 1-(2-N,N-dimethylaminoethyl)-1-oxo-1,2,3,4-tetrahydrophosphinoline.

3. The compound 1-(2-N,N-dimethylaminoethyl)-1-thio-1,2,3,4-tetrahydrophosphinoline.

4. The compound 1-(2-N,N-dimethylaminoethyl)-phosphindoline 1-oxide.

5. The compound 1-(2,N,N-dimethylaminoethyl)-phosphindoline 1-sulphide.

6. The compound 1-(2-pyrrolidinoethyl)-1-oxo-1,2,3,4-tetrahydrophosphinoline.

7. The compound 1-(2-pyrrolidinoethyl)-1-thio-1,2,3,4-tetrahydrophosphinoline.

8. The compound 1-(2-piperidinoethyl)-1-thio-1,2,3,4-tetrahydrophosphinoline.

* * * * *